(12) United States Patent
Kumar et al.

(10) Patent No.: US 8,460,178 B2
(45) Date of Patent: Jun. 11, 2013

(54) METHOD AND SYSTEM FOR MINIMIZING LEAKAGE OF A DISTENDING MEDIUM DURING ENDOSCOPIC PROCEDURES

(76) Inventors: Atul Kumar, Jaipur (IN); Alka Kumar, Jaipur (IN)

( * ) Notice: Subject to any disclaimer, the term of this patent is extended or adjusted under 35 U.S.C. 154(b) by 347 days.

(21) Appl. No.: 11/280,734

(22) Filed: Nov. 17, 2005

(65) Prior Publication Data

US 2006/0264701 A1 Nov. 23, 2006

(30) Foreign Application Priority Data

Nov. 30, 2004 (IN) .......................... 2392/DEL/2004

(51) Int. Cl.
*A61B 1/04* (2006.01)
*A61M 5/00* (2006.01)

(52) U.S. Cl.
USPC ........... 600/115; 600/114; 600/116; 600/127; 604/271

(58) Field of Classification Search
USPC .. 600/115, 116, 127, 114, 121, 124; 128/898; 604/264, 271, 528, 276
See application file for complete search history.

(56) References Cited

U.S. PATENT DOCUMENTS

| | | | | |
|---|---|---|---|---|
| 3,797,478 A * | 3/1974 | Walsh et al. | ..................... | 600/29 |
| 3,978,531 A * | 9/1976 | Ilon | ................. | 5/81.1 T |
| 4,207,872 A * | 6/1980 | Meiri et al. | ..................... | 600/116 |
| 4,228,792 A * | 10/1980 | Rhys-Davies | .................. | 601/19 |
| 4,868,967 A * | 9/1989 | Holt et al. | ....................... | 29/450 |
| 5,045,070 A * | 9/1991 | Grodecki et al. | ............. | 604/271 |
| 5,070,597 A * | 12/1991 | Holt et al. | ........................ | 29/887 |
| 5,236,423 A * | 8/1993 | Mix et al. | ...................... | 600/115 |
| 5,470,314 A * | 11/1995 | Walinsky | ................. | 604/103.11 |
| 5,545,179 A | 8/1996 | Williamson, IV | | |
| 5,571,114 A * | 11/1996 | Devanaboyina | .................. | 606/1 |
| 5,803,921 A | 9/1998 | Bonadio | | |
| 5,964,781 A * | 10/1999 | Mollenauer et al. | .......... | 606/213 |
| 6,200,288 B1 * | 3/2001 | Heaton et al. | .................... | 604/59 |
| 6,234,958 B1 * | 5/2001 | Snoke et al. | ................... | 600/114 |
| 6,468,292 B1 * | 10/2002 | Mollenauer et al. | .......... | 606/213 |
| 6,479,000 B2 * | 11/2002 | Conway et al. | ............... | 264/135 |
| 6,695,816 B2 * | 2/2004 | Cassidy, Jr. | .............. | 604/165.02 |
| 6,953,431 B2 * | 10/2005 | Barthel | .......... | 600/115 |
| 6,971,990 B2 * | 12/2005 | Ziegler et al. | ................. | 600/114 |
| 7,060,086 B2 * | 6/2006 | Wilson et al. | ................. | 607/114 |
| 7,563,250 B2 * | 7/2009 | Wenchell | ................. | 604/167.01 |
| 7,621,944 B2 * | 11/2009 | Wilson et al. | ................. | 607/108 |
| 7,708,687 B2 * | 5/2010 | Bern et al. | ..................... | 600/115 |
| 2002/0016607 A1 | 2/2002 | Bonadio et al. | | |
| 2002/0072762 A1 * | 6/2002 | Bonadio et al. | .............. | 606/192 |
| 2003/0114803 A1 * | 6/2003 | Lerner | .......... | 604/276 |
| 2004/0092795 A1 * | 5/2004 | Bonadio et al. | .............. | 600/207 |
| 2004/0097793 A1 | 5/2004 | Butler et al. | | |
| 2004/0162531 A1 | 8/2004 | Wenchell | | |

(Continued)

FOREIGN PATENT DOCUMENTS

IE 20020945 A * 7/2003

*Primary Examiner* — Philip R Smith
*Assistant Examiner* — Rynae Boler
(74) *Attorney, Agent, or Firm* — Dickstein Shapiro LLP

(57) ABSTRACT

A system for minimizing leakage of fluid distending media by the sides of the endoscopic instrument in endoscopic procedures such as arthroscopy, hysteroscopy or laparoscopy. A double-wall flexible tubular sheath having walls containing pressurized fluid is mounted over an endoscopic instrument. The double-wall flexible tubular sheath moves in and out of a natural opening of a tissue cavity or through an incision made in the cavity wall.

13 Claims, 7 Drawing Sheets

U.S. PATENT DOCUMENTS

| | | | |
|---|---|---|---|
| 2004/0186349 A1* | 9/2004 | Ewers et al. | 600/114 |
| 2006/0020164 A1* | 1/2006 | Butler et al. | 600/115 |
| 2008/0045790 A1* | 2/2008 | Ziegler et al. | 600/114 |
| 2008/0058596 A1* | 3/2008 | Bob et al. | 600/114 |
| 2009/0043159 A1* | 2/2009 | Dumot | 600/114 |

* cited by examiner

METHOD AND SYSTEM FOR MINIMIZING LEAKAGE OF A DISTENDING MEDIUM DURING ENDOSCOPIC PROCEDURES

FIELD OF THE INVENTION

The present invention relates to a system which avoids or minimizes leakage of a distending liquid or gaseous medium by the sides of an endoscopic instrument during endoscopic procedures, such as arthroscopic, hysteroscopic or laparoscopic surgery.

BACKGROUND OF THE INVENTION

Endoscopic surgery is becoming increasingly popular because it is a minimally invasive form of surgery, it is associated with less pain, and the patients can return back to normal work relatively early with minimal loss of working days.

In endoscopic surgeries, an endoscope is typically introduced into a body cavity via the natural opening of the cavity or, alternatively, a minute hole is made in the wall of the cavity through which the endoscope is introduced to visualize the interior of the body tissue cavity and to perform endoscopic surgical procedures. For the purposes of the present invention, the term "tissue cavity opening" shall be used to refer to a natural opening of a body tissue cavity opening, via which an endoscopic instrument is introduced. Additionally, the term "tissue cavity opening" shall be used to refer to an incision or hole made in the tissue cavity for passing an endoscopic instrument. For these reasons, endoscopic surgery is also referred to as "key hole" or "minimal access" surgery.

Endoscopic surgery is primarily related to a tissue cavity. Most endoscopic surgical procedures are carried out on an existing body cavity which is distended or "ballooned up" by filling the cavity with a suitable distending medium, which permits the inner lining of the tissue cavity to be visualized through an endoscope. Hysteroscopy, arthroscopy and laparoscopy are only a few of the routinely performed endoscopic procedures.

In its natural state, a tissue cavity is a collapsed structure with the cavity walls being in apposition with each other as if kissing each other. Accordingly, if an endoscope is introduced in such a collapsed cavity, no endoscopic visualization is possible unless the cavity is ballooned up by filling it with a transparent fluid. Such ballooning of the tissue cavity is called "cavity distension." No endoscopic procedure can be performed if an adequate distension of the tissue cavity is not achieved and maintained. Cavity distension provides both endoscopic visualization and mechanical distension, which are necessary for the manipulation of endoscopic instruments.

Besides many other criteria related to patient safety and surgical accuracy, an efficient cavity distension is one in which the distending medium does not leak by the sides of an endoscopic instrument. If leakage occurs, the tissue cavity collapses and adequate mechanical separation of the cavity walls cannot be achieved and the mechanical separation cannot be maintained, thus making endoscopic surgery difficult or impossible. Accordingly, it is extremely important to prevent the leakage of the distending medium by the sides of an endoscopic instrument.

For a better understanding of the present invention, a brief description of the basic physics of cavity distension is provided below. Filling the tissue cavity with fluid enables distension of the cavity. Initially, more fluid is pumped than the amount which is extracted from the cavity and, ultimately, the inflow rate is fixed at a level where a desired cavity pressure and distension is achieved. This is termed distension by using "continuous flow irrigation." However, a cavity can also be distended by using the less preferred "non continuous flow irrigation," wherein the cavity is distended by simply instilling fluid into a cavity while there is no outflow tube. This distension by "non continuous flow irrigation" can also be termed "distension by utilizing a static type system." In laparoscopic surgery, the abdominal cavity is only distended by instilling carbon dioxide by the static type of system. Irrespective of the type of distension technique utilized, i.e., distension by "continuous flow irrigation" or distension by using a "static type system," it is important to avoid or at least minimize the leakage of the distending medium by the sides of the endoscopic instrument.

An endoscope is a cylindrical tube having an outer diameter ranging between 3 to 9 mm approximately. A typical endoscope has four channels. One channel allows passage of a fiber optic telescope while endoscopic instruments are inserted through a second channel. A third channel, also known as the "inflow channel," is used for introducing irrigation fluid into a tissue cavity, the proximal end of this channel ending in a metal adaptor known as the "inflow port," while the distal end of this inflow channel opens near the tip of the endoscope. The inflow port is connectable to an inflow tube which carries sterile irrigation fluid from a fluid source reservoir. A fourth channel, also known as the "outflow channel," allows extracting the waste fluid out of the cavity, the proximal end of this channel ending in a metal adaptor known as the "outflow port," while the distal end of this outflow channel opens near the tip of the endoscope. The outflow port is connectable with an outflow tube which transports the waste fluid from the cavity to a suitable waste fluid collecting reservoir. However, in the static distension system, the outflow port and the outflow channel are missing or not used in the endoscope, and either gas or fluid can be instilled via the inflow channel of the endoscope. A set of fiber optic bundles contained inside the telescope transmit light energy produced by an external light source. This light energy illuminates the walls of the tissue cavity. The image thus formed is carried via a separate set of optical pathways situated inside the telescope. A video camera attached to the eye piece of the telescope forms a clear endoscopic image of the cavity on a TV monitor. The surgeon has to continuously look at the TV monitor all through the endoscopic procedure.

A brief description of a distending medium leak occurring by the sides of an endoscope of the prior art is described below. The fluid of gaseous medium which distends a tissue cavity is pressurized and, thus, it may leak by escaping through a potential space located between the endoscope and the tissue cavity opening, if a liquid tight or a gas tight contact is not present between the endoscope and the tissue cavity opening. Such leakage is undesirable and, thus, the terms "cavity leak" and "cavity leakage" (which are used interchangeably) refer to leakage of a distending liquid or gas by the sides of an endoscope, including endoscopic surgical instruments that could enter into the tissue cavity through a cannula or which may be introduced directly (that is without a cannula). The surgical instruments could be shavers, endoscopic forceps, endoscopic scissors, endoscopic tissue retractors, probes and electrodes, among others. Thus, for the purposes of the present invention, the terms "endoscope" and "endoscopic instrument" are used interchangeably, and these terms are intended to include all surgical instruments whether passed directly or through a cannula.

The mechanism and causes of "cavity leakage" are different for different type of endoscopic procedures. Accordingly, a separate discussion for each type of endoscopic procedure is provided below.

In arthroscopic surgery, a trocar cannula is initially introduced into a joint cavity and subsequently the trocar is removed from the cannula to allow an endoscopic instrument to be introduced in place of the trocar. The trocar cannula consists of a trocar contained inside a cannula, which is a hollow rigid, usually metallic, cylindrical tube. The trocar is a long solid cylindrical rod, usually metallic, having a pointed or a relatively blunt distal end. A small incision is made in the skin overlying the joint cavity, and the trocar cannula is inserted into the joint cavity by using the pointed end of the trocar. The initial incision created by the pointed tip of the trocar is subsequently dilatated by the dilated proximal part of the trocar. The telescope is usually housed in a portal created in the manner just described. A separate portal may also be made in a similar manner to house an outflow tube via which waste fluid would be removed from the joint cavity. A shaver, especially for treatment of a shoulder joint, may also be passed via a portal incorporating a cannula as already described.

Alternatively, in certain situations such as the knee joint, a shaver may be directly introduced into the joint cavity without using the cannula. For this, a slit is first made in the capsule wall through which the shaver is directly inserted into the joint cavity. Especially at higher intra articular pressures, the distending fluid may leak around the sides of the shaver or around the sides of other endoscopic instruments inserted into the joint cavity. Such leakage is undesirable as it leads to a reduction in the intra articular pressure, which necessitates a greater inflow rate in order to maintain the same intra articular pressure. In addition, if a peristaltic pump is used, for example, on the inflow side, such increased flow rate could culminate in an increased frequency and amplitude of the cavity pressure pulsations caused by the peristaltic pump, which will ultimately lead to an increased turbulence inside the joint cavity. The cavity leak could also lead to a fluid leakage on the floor, it could also cause extracapsular extravasation of fluid, and it could also impede a surgeon from correctly calculating the total volume of fluid extravasation, as there is no reliable method of measuring the total volume of fluid which spills on the floor. The cavity leakage could also occur if two endoscopes having different outer diameters were interchanged.

In laparoscopic surgery, the carbon dioxide gas used for distending the abdominal cavity may at times leak around the sides of the endoscope, especially if two endoscopes having different outer diameters are interchanged. Such a leak can also occur if the initial slit given over the fascia, to facilitate the insertion of the trocar cannula, is relatively larger than required.

In hysteroscopic surgery, fluid might leak through a space present between the hysteroscope and the cervical os, especially if the cervical os is accidentally over dilated or if the cervical os is wide open right from the beginning of the surgery. The term "cervical os" refers to the natural opening of a woman's uterus. Such cavity leakage could make hysteroscopic surgery difficult as well as dangerous.

Methods for avoiding or minimizing cavity leakage are desirable as they would make the endoscopic procedures easier, safer and would also help in conserving costly distending fluid. A method for preventing or minimizing such leakage is to install a plastic or metallic sheath permanently over the endoscope. Such sheath must not be allowed to slip or to get detached from the endoscope. In physical terms, incorporation of the sheath results in an increase in the effective outer diameter of the endoscope, which reduces or avoids cavity leakage by developing a watertight or a gastight contact between the endoscope and the tissue cavity opening. However, it is impractical and difficult to use such sheaths and the result, in terms of minimizing or avoiding cavity leakage, is also unpredictable.

Further, if endoscopes must be interchanged during the course of an endoscopic procedure, it is inconvenient, from a practical standpoint, to remove and then install a sheath having a different outer diameter. The incorporation of the sheaths also restricts the maneuverability of the endoscope, thereby requiring greater force to move the endoscope in a to and fro, or rotary, motion.

Accordingly, a need exists for a system which would help in avoiding or minimizing the leakage of a gaseous or liquid distending medium through a space located between an endoscopic instrument and a corresponding tissue cavity opening, so that the maneuverability of the endoscopic instrument is not compromised.

SUMMARY OF THE INVENTION

The present invention overcomes disadvantages of the prior art, such as those noted above, by providing a system for reducing or minimizing the leakage of a liquid or gaseous distending medium on at least one side of an endoscopic instrument. The present invention also provides a method for allowing two endoscopic instruments having different outer diameters to be interchanged without the risk of liquid or gaseous leak. A method of preventing an endoscopic instrument from accidentally slipping out of a tissue cavity, or from accidentally traversing beyond any desired depth inside a tissue cavity, is also provided.

The present invention also provides a method for regulating the leakage of a distending medium, by increasing or decreasing such leakage of the distending medium. An endoscopic instrument with enhanced maneuverability is also provided.

Other features and advantages of the present invention will become apparent from the following description of the invention, which refers to the accompanying drawings.

DETAILED DESCRIPTION OF THE PREFERRED EMBODIMENTS

Figure 1:
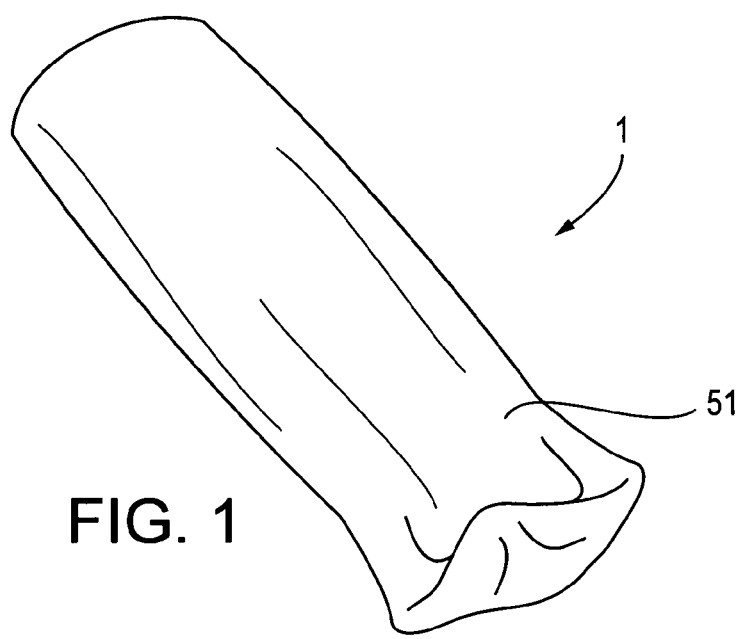
FIG. 1 is a photograph of a flexible tubular sheath which is employed with a distending medium management system of the present invention.

The term "flexible tubular sheath" as used in the present invention is intended to encompass any double-wall hollow body which is open at both ends and which is filled with a fluid, either a liquid or gas, or a combination of a liquid and gas. The term "flexible tubular sheath" also refers to a flexible containment structure whose walls are made of a strong, relatively thick elastic distensible material, such that the cavity could be filled with only a maximum predetermined volume of liquid or gas beyond which the cavity pressure would rise steeply and the structure would burst. As used in the present invention, the term "flexible tubular sheath" is not limited to a tube, or to a tube having a cylindrical or oval cross-section, but rather the term "flexible tubular sheath" is intended to encompass a structure that has an inner hollow body defined by double walls and filled with a liquid or gas, or a combination of liquid or gas.

The terms "tissue cavity opening" and "cavity opening" as used in the present invention are interchangeable, and they are intended to encompass a natural opening of a body tissue cavity opening, via which an endoscopic instrument may be introduced. The terms "tissue cavity opening" and "cavity opening" also refer to an incision or hole made in a tissue cavity for passing an endoscopic instrument.

The term "rigid thickening" as used in the present invention is intended to encompass any rigid or partially rigid portion that is attached to, affixed to, or integral with, at least a flexible portion of the "flexible tubular sheath" as defined above.

Although the present invention will be described below with reference to an endoscopic instrument having a rigid cylindrical tube which is introduced into a tissue cavity, the invention is not limited to this embodiment and contemplates embodiments which utilize an endoscopic instrument that is flexible, or any other endoscopic instruments that are partially rigid or partially flexible.

The terms "cavity leak" and "cavity leakage" are used interchangeably in the present invention and they refer to leakage of a distending liquid or gas by the sides of an endoscopic surgical instrument that could enter into the tissue cavity through a cannula or which may be introduced directly (that is without a cannula).

The terms "endoscope" and "endoscopic instrument" are used interchangeably in the present invention, and these terms are intended to include all surgical instruments whether passed directly or through a cannula into a tissue cavity.

Referring now to the drawings, where like elements are designated by like reference numerals, FIGS. 1-5 illustrate a flexible tubular sheath 1 of the present invention which is used in connection with an endoscopic instrument as part of distending medium management system 100 (FIGS. 6A-10D) of the present invention.

Flexible tubular sheath 1 of FIGS. 1-5 comprises a double-wall hollow body, open at both ends, which is filled with a pressurized liquid or a gas 51. The cylindrical body of the present invention is open at both ends. Walls 53 of the flexible tubular sheath 1 are not solid, but are rather double-walled containing pressurized liquid or gas. In an exemplary embodiment, walls 53 are made of an elastic material, for example, a distensible elastic polymeric material. The double-wall body would lose its shape if the liquid or gas 51 (or a combination of liquid and gas) contained in it were to be totally or partially removed.

Figure 2A:
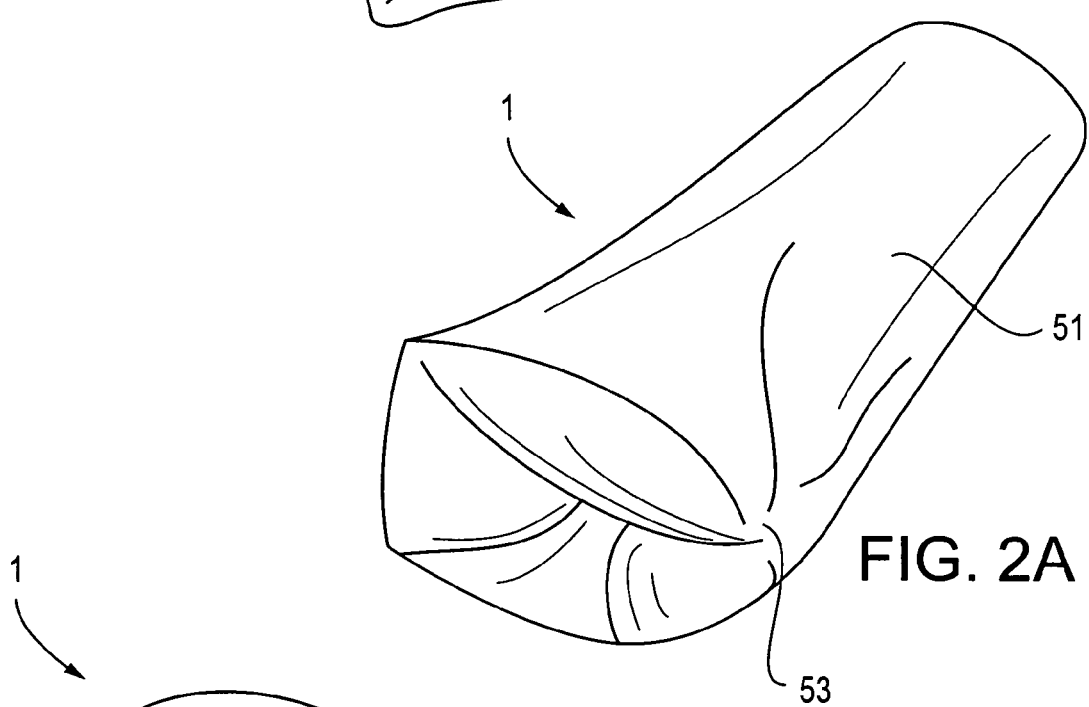
FIG. 2A illustrates another view of the flexible tubular sheath of FIG. 1.
Figure 2B:
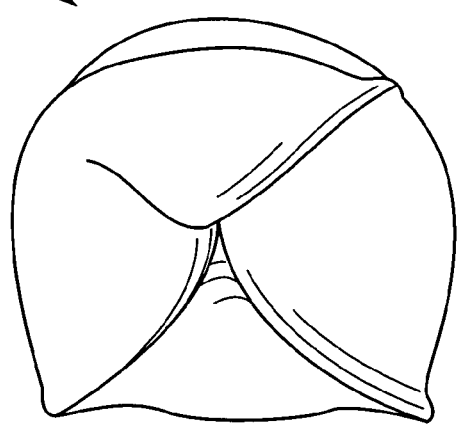
FIG. 2B illustrates an end view of the flexible tubular sheath of FIG. 1.

The flexible tubular sheath 1 of FIG. 1 is similar to a squeezable plastic object which is ordinarily sold as a toy for children. As shown in FIGS. 1, 2A and 2B, the flexible tubular sheath 1 is a hollow cylindrical tube, open at both ends, the walls of which are filled with fluid. When children hold this toy in their hands, the toy quickly rolls out of their hands and falls on the floor. Thus, it is difficult to hold this toy as it easily rolls out of the hands and this is one of the reason that children enjoy playing with such a toy.

It is important to note that, similar to the toy with which children play, the flexible tubular sheath of the present invention only "rolls" out of the hands and does not "slip" out of the hands. There is a difference between "rolling" and "slipping." If the flexible tubular sheath was a conventional solid metallic cylindrical steel rod, then it could only slip out of the hands to fall on the floor. However, such solid structure could not roll out of the hands like the flexible tubular sheath shown in FIGS. 1, 2A and 2B.

Figure 3:
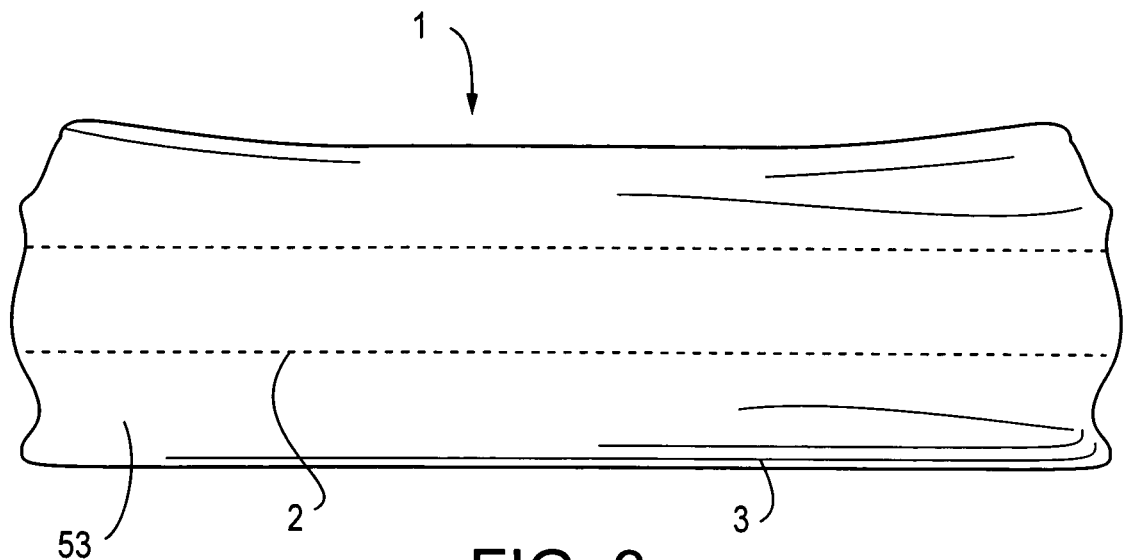
FIG. 3 illustrates the flexible tubular sheath of FIG. 1 with the inner surface shown in dashed lines.

FIGS. 2A and 2B show the flexible tubular sheath 1 from two different angles. FIG. 3 shows the same flexible tubular sheath 1 but with the inner surface of the flexible tubular sheath shown by dashed lines 2. The outer surface of the flexible tubular sheath is labeled as reference numeral 3.

Figure 4:
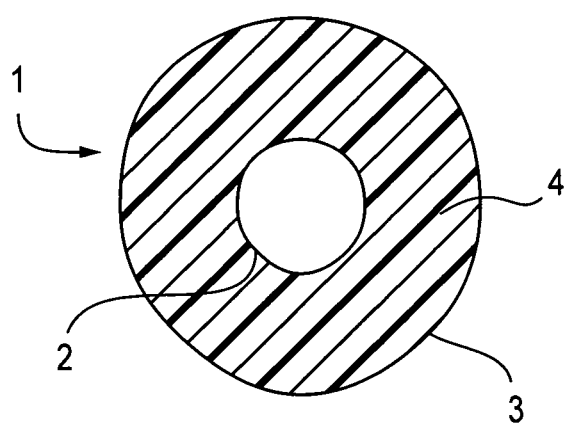
FIG. 4 illustrates a schematic cross-sectional view of the flexible tubular sheath of FIG. 1.
Figure 5:
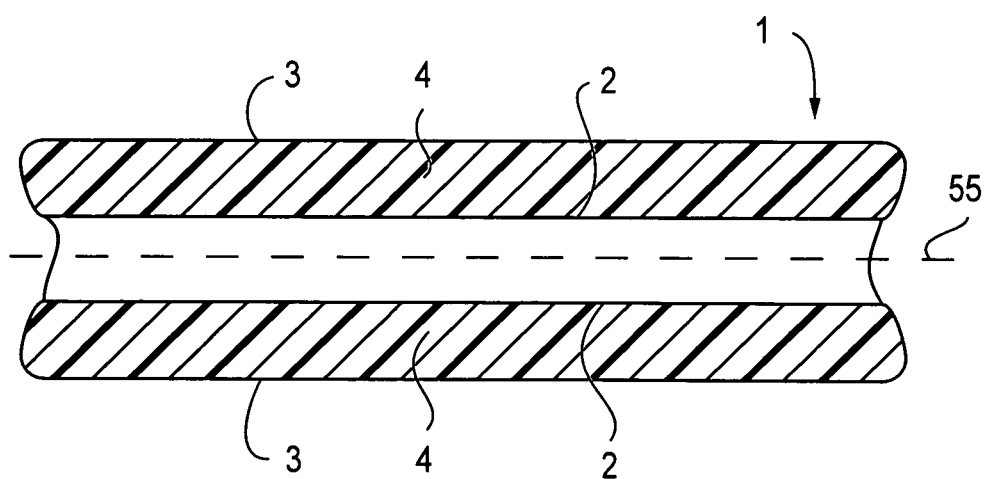
FIG. 5 illustrates a saggital section of the flexible tubular sheath of FIG. 1.

FIG. 4 is a line diagram showing a cross-sectional view of the flexible tubular sheath 1, the cross-sectional view having been cut perpendicular to the long axis 55 of the flexible tubular sheath. The outer and inner surfaces of the flexible tubular sheath have been labeled as reference numerals 3 and 2, respectively. The closed cavity contained between the inner and the outer surface is labeled 4. FIG. 5 is a line diagram showing the cut section of the flexible tubular sheath 1 along the sagittal plane of the flexible tubular sheath. The outer and inner surfaces of the flexible tubular sheath have been labeled as reference numerals 3 and 2, respectively. The closed cavity contained between the inner and the outer surface is labeled as reference numeral 4.

Figure 6A:
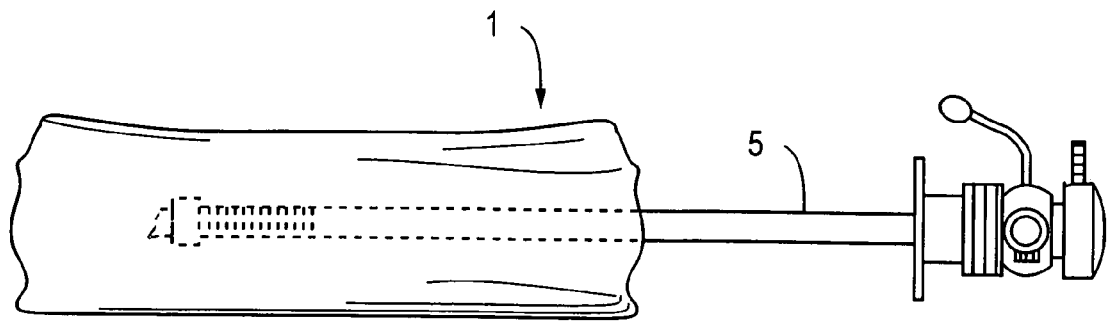
FIG. 6A illustrates the flexible tubular sheath of FIG. 1 provided over a distal end of an endoscopic instrument and as part of a distending medium management system of the present invention.
Figure 6B:
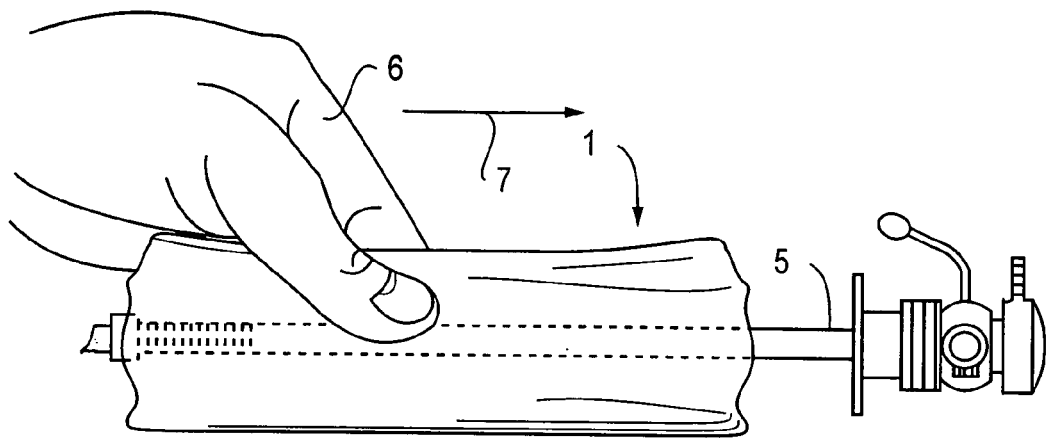
FIG. 6B illustrates the flexible tubular sheath of FIG. 6A positioned towards the proximal end of the endoscopic instrument.
Figure 6C:
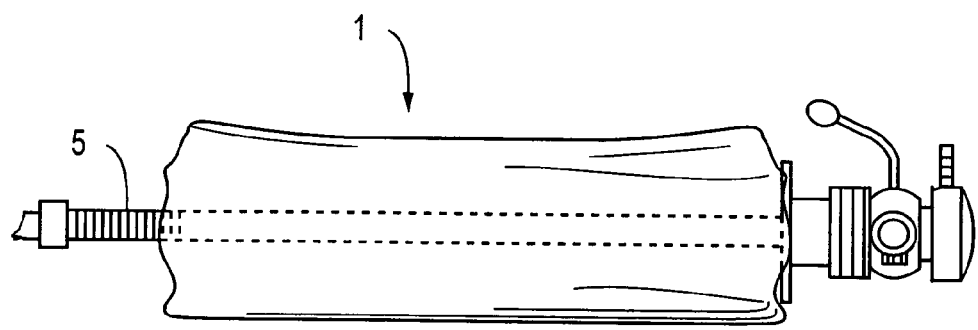
FIG. 6C illustrates the flexible tubular sheath of FIG. 6B positioned at the proximal end of the endoscopic instrument.

FIG. 6A shows flexible tubular sheath 1 disposed over the distal part of the endoscopic instrument 5. In FIG. 6B, the flexible tubular sheath is shown grasped by a hand 6 which attempts to push the flexible tubular sheath towards the proximal end of the endoscopic instrument in the direction of arrow 7. It is assumed that the inner surface 2 of the flexible tubular sheath is stretched over the endoscopic instrument 5 so that the inner surface 2 maintains a sufficiently tight grip on the endoscopic instrument 5 such that, when the hand 6 attempts to push the containment system 1 in the direction of the arrow 7, the flexible tubular sheath can only move by rolling in the direction of arrow 7. FIG. 6C shows the flexible tubular sheath 1 over the proximal end of the endoscopic instrument.

Figure 7A:
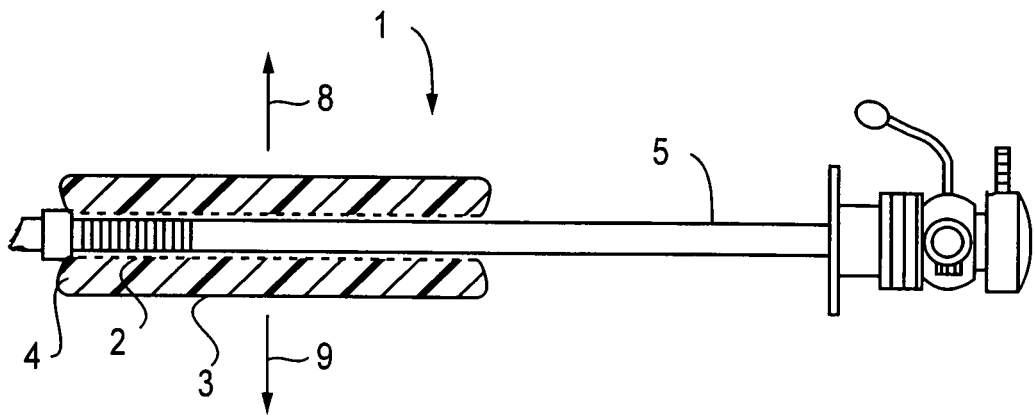
FIG. 7A illustrates a saggital section through the flexible tubular sheath and the distal end of the endoscopic instrument of FIG. 6A.
Figure 7B:
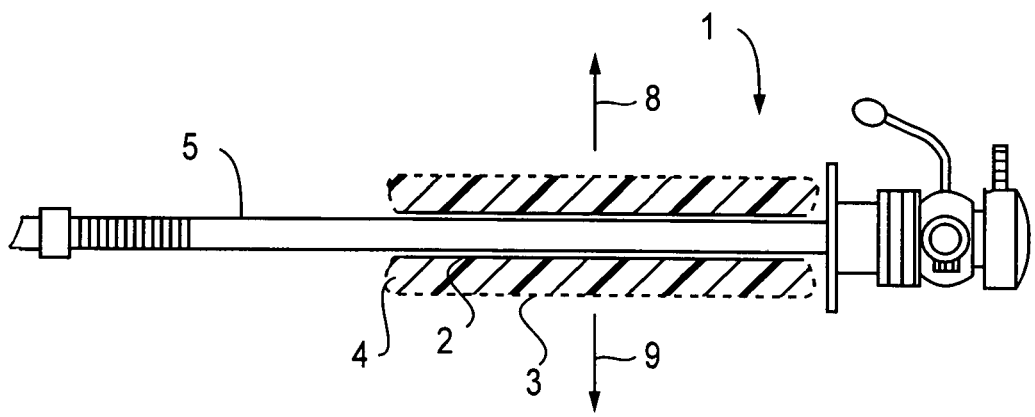
FIG. 7B illustrates a saggital section through the flexible tubular sheath and the proximal end of the endoscopic instrument of FIG. 6C.

In FIG. 7A, the inner surface of the flexible tubular sheath fits snugly and tightly over the endoscopic instrument 5 and is denoted by a thin dashed line 2, while the outer surface 3 is denoted by a thick line 3. In FIG. 7B, the inner surface is denoted by a thick line 2, while the outer surface is denoted by a thin dashed line 3. Referring to FIG. 6B, when the flexible tubular sheath 1 is pushed by hand 6, the flexible tubular sheath could get displaced in the direction of the arrow 7 only by a rolling motion and not by virtue of its inner surface slipping over the external metallic surface of the endoscopic instrument, because the inner surface 2 is assumed to be tightly stretched over the endoscopic instrument 5.

Referring back to FIG. 7B, the surfaces have interchanged their positions in comparison to FIG. 7A, and the same has been made possible by the rolling motion exhibited by the flexible tubular sheath 1. As the walls of the flexible tubular sheath 1 are made of a distensible elastic material, the inner surface 2 fits snugly and tightly over the endoscopic instrument 5 by virtue of the elasticity of the distensible elastic material and also by virtue of the positive pressure inside the cavity 4. Cavity 4 is a closed cavity contained between the outer and inner surfaces of the flexible tubular sheath. As explained later, it is the inherent elasticity of the distensible elastic material which causes the inner surface 2 of the flexible tubular sheath to snugly fit tightly over the endoscopic instrument 5, while the positive pressure inside the cavity 4 may also contribute.

The flexible tubular sheath 1 of FIG. 1 comprises a thin distensible elastic polymeric material having substantial elasticity and a substantial distensibility, which means that the total volume of the cavity 4 could be increased substantially if additional liquid or gas was somehow introduced into the cavity 4. However, as explained below, this is undesirable for the present invention. Referring to FIGS. 7A and 7B, if additional liquid or gas was introduced inside the cavity 4, the outer surface of the flexible tubular sheath would expand in the direction of arrows 8 and 9, while the inner surface 2 would continue to remain tightly fitted over the endoscopic instrument 5. The system of the present invention requires that the inner surface 2 remain tightly fitted over the endoscopic instrument, mainly by virtue of its inherent elasticity, while the positive pressure inside the cavity 4 could contribute by a limited extent. The flexible tubular sheath walls need to be formed of a sufficiently thick, strong and elastic polymeric material, such that the cavity 4 had a limited maximum distensibility.

For the purpose of the present invention, the term "limited maximum distensibility" refers to the fact that it should not be possible to inflate the cavity 4 like a balloon, which could be inflated to a substantial volume. In the context of the present invention, the walls of the flexible tubular sheath cavity should be sufficiently thick and strong, such that after minimal volume of liquid or gas is introduced inside the flexible tubular sheath cavity 4, the cavity should start increasing steeply so that the cavity would burst if more fluid was to be introduced. The maximum cavity pressure attained before the burst in a manner explained above would depend upon the overall strength and thickness of the polymeric material constituting the cavity wall. Thus, for the purpose of the present invention, the term "flexible tubular sheath" refers to a flexible containment structure whose walls are made of a strong, relatively thick elastic distensible material, such that the cavity 4 could be filled with only a maximum predetermined volume of liquid or gas beyond which the cavity 4 pressure would rise steeply. For the system of the present invention, the flexible tubular sheath cavity could be filled by both liquid or gas, or a combination of liquid and gas.

As shown in FIGS. 1, 2A, 2B, 3, 6A, 6B, 6C and 9, the flexible tubular sheath has two ends which look similar. However, in relation to an endoscopic instrument, the flexible tubular sheath has a distal end and a proximal end. Referring to FIGS. 7A and 7B, the flexible tubular sheath has two ends, the end near to the tip of the endoscopic instrument 5 is being termed as the "distal end" and the part of the flexible tubular sheath nearest to the proximal part of the endoscopic instrument (that is, the part of the endoscopic instrument which always remains outside the tissue cavity) is termed the "proximal end" of the flexible tubular sheath.

It could be difficult to install the flexible tubular sheath over the endoscopic instrument, especially if the flexible tubular sheath were to be made of a strong thick distensible elastic polymeric material. Thus, by suitable mechanical means, and in accordance with the present invention, a non-distended flexible tubular sheath is initially installed over a plastic or metallic hollow cylindrical tube whose inner diameter is greater than the outer diameter of the endoscopic instrument 5. The plastic or metallic tube for housing the flexible tubular sheath is termed "flexible tubular sheath applicator" (not shown). The flexible tubular sheath applicator also has two ends, a proximal end and a distal end. The proximal flexible tubular sheath applicator end corresponds to the prospective proximal flexible tubular sheath end, while the distal flexible tubular sheath applicator end corresponds to the prospective distal flexible tubular sheath end.

The endoscopic instrument 5 is inserted into the flexible tubular sheath applicator so that the proximal end of the flexible tubular sheath applicator contacts the proximal part of the endoscopic instrument. Subsequently, the proximal end of the flexible tubular sheath is strongly held and anchored via suitable mechanical means, while the distal end of the flexible tubular sheath applicator is pulled away distally, in a direction away from the tip of the endoscopic instrument. Upon completion of such maneuver, the flexible tubular sheath snugly and tightly fits over the endoscopic instrument. As explained in more detail below, the flexible tubular sheath has to be installed on a specific location over the endoscopic instrument. Thus, it could be helpful if the length of the flexible tubular sheath applicator was equal to the length of the endoscopic instrument so that, when the proximal end of the flexible tubular sheath applicator touched the proximal end of the endoscopic instrument, the distal flexible tubular sheath end was in exact apposition with the distal end, i.e., the tip opening of the endoscopic instrument. Thus, in a preferred embodiment, deflated flexible tubular sheath is initially housed over a predetermined location over the flexible tubular sheath applicator, so that the flexible tubular sheath could ultimately be transferred to a predetermined specific location over the endoscopic instrument.

The distending medium management system 100 of the present invention requires that the endoscopic instrument, with the flexible tubular sheath attached to it, roll through a tissue cavity opening and never be forced to slip through the tissue cavity opening. If the containment system, instead of rolling, would be made to slip in a to and fro direction through the tissue cavity opening, this would require the flexible tubular sheath cavity 4 to be filled with a relatively greater volume of fluid such that an adequate indentation on the outer surface of the flexible tubular sheath, which facilitates the rolling motion, is not allowed to develop. In this situation, the entire outer surface 3 would have a substantial permanent convexity due to which the flexible tubular sheath could only slip and not roll. The point of maximum convexity would be at the mid point of the flexible tubular sheath along its long length. However, this would create problems. The leak would not be properly sealed while the proximal or the distal ends of the flexible tubular sheath were in contact with the tissue cavity opening because proximal or the distal ends of the flexible tubular sheath would have a relatively smaller outer diameter in comparison to the central point of maximum convexity. It could be relatively more difficult to move the endoscopic instrument in a to and fro direction while the mid part of the flexible tubular sheath was in apposition with the tissue cavity opening, due to mechanical resistance. The point of maximum convexity could also lacerate or over-dilate the tissue cavity opening.

In physical terms, if a relatively over-distended flexible tubular sheath is made to slip through the tissue cavity opening, the force of indentation which develops between the outer surface of the flexible tubular sheath and the inner surface of the tissue cavity opening varies during a linear to and fro movement. The force is maximum while the central part having maximum convexity is in apposition with the tissue cavity opening and minimum when the two ends of the flexible tubular sheath participate in apposition. Thus, the surgeon would have to apply a variable force while moving the endoscopic instrument in a to and fro direction, if the flexible tubular sheath were to slip instead of roll. For these reasons, the flexible tubular sheath should never be allowed to slip in and out of the cavity, but instead it should be allowed to exhibit a rolling motion. Even if the convexity of the flexible tubular sheath were to be minimized by using a thicker and a stronger polymeric material, considerable friction could be encountered if the flexible tubular sheath was made to slip through the tissue cavity opening.

The cavity 4 could be pre-filled with an adequate volume of fluid, the volume being less than the maximum volume of fluid which the cavity 4 can conveniently accommodate. The concept of "maximum flexible tubular sheath cavity volume" is discussed below. When such a partially distended flexible tubular sheath enters into the tissue cavity opening, the distal end of the flexible tubular sheath cavity 4 collapses after being squeezed by the inner surface of the tissue cavity opening, thus some small volume of fluid from the distal end of the flexible tubular sheath cavity 4 enters into a proximal part of the flexible tubular sheath cavity 4, thus increasing the overall size of the proximal part of the flexible tubular sheath cavity. This allows a relatively more tight contact between the tissue cavity opening and the outer surface of the flexible tubular sheath, which helps in initiating a rolling motion for the flexible tubular sheath. However, if the flexible tubular sheath repeatedly rolls in a to and fro direction, the outer surface of the flexible tubular sheath may accidentally slip over the tissue cavity opening instead of rolling. The unwanted accidental slipping could occur more frequently if the flexible tubular sheath cavity was filled with an inadequate volume of fluid. Such slipping may result in the flexible tubular sheath being completely detached from the endoscopic instrument in a distal direction, or the flexible tubular sheath may even be displaced to an extreme proximal position with respect to the endoscopic instrument, and in such a situation the leakage may no longer be minimized. The solution to this problem is set forth in the following paragraph.

Figure 8A:
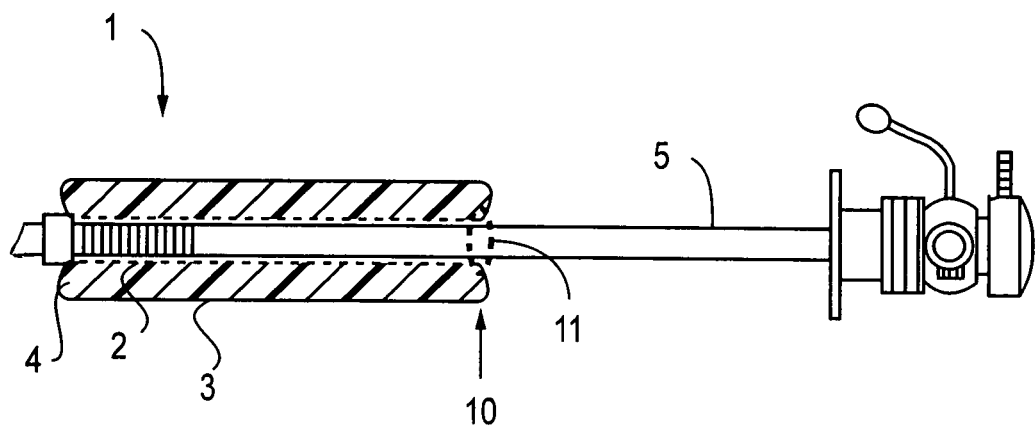
FIG. 8A illustrates a cross-sectional view of the flexible tubular sheath of FIG. 7A with a rigid thickening located at the most proximal end of the toy.
Figure 8B:
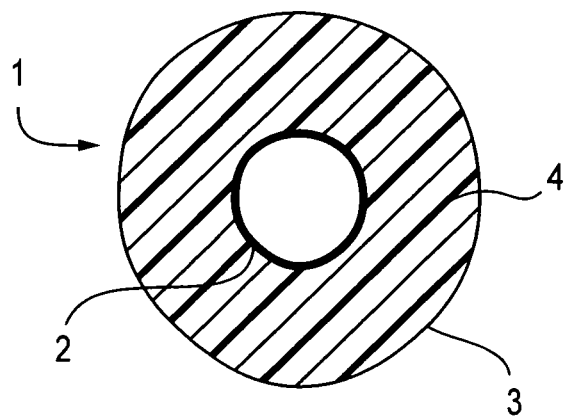
FIG. 8B illustrates a cross-sectional view of the rigid thickening of FIG. 8A.

Referring to FIGS. 8A and 8B a "rigid thickening" or "rigid portion" could be introduced on the inner surface 2 of the flexible tubular sheath along a transverse plane at right angles to the long length of the flexible tubular sheath. In an exemplary embodiment, the rigid thickening of the present invention could be in the form of a non-stretchable, sufficiently strong thread impregnated in the wall of the inner surface near its proximal end. In another exemplary embodiment, the rigid thickening of the present invention may be a thin metallic wire. In yet another exemplary embodiment, the rigid thickening may also be a localized circular thickening of the polymeric material constituting the flexible tubular sheath wall. The part of the inner surface which is in contact with the thickening resists any distension due to the rigid thickening. As suggested by the term "rigid thickening," the flexible tubular sheath cannot distend along the point of attachment or impregnation with the rigid thickening.

Referring to FIG. 8A, the rigid thickening is located at a point 10. The rigid thickening is denoted by a dotted oval line 11. The location of point 10 depends upon the length of the flexible tubular sheath and the overall length of the endoscopic instrument. When the flexible tubular sheath is introduced by the flexible tubular sheath applicator on the endoscopic instrument, the rigid thickening should be located at the most proximal end of the flexible tubular sheath. FIG. 8B shows a cross-sectional view at point 10 wherein the rigid thickening is denoted by a thick circular line 2. Referring to FIG. 8A, the flexible tubular sheath cannot roll in a distal direction because the rigid thickening does not allow the same. Again, referring to FIG. 8A, the location of point 10 is chosen so that the distal most part of the flexible tubular sheath just falls short of the tip of the endoscopic instrument. The rigid thickening 11 does not allow the flexible tubular sheath to become detached from the endoscopic instrument. The rigid thickening 11 helps in firmly anchoring the flexible tubular sheath to the endoscopic instrument, such that the flexible tubular sheath never slips in a distal direction with respect to the distal end of the endoscopic instrument.

Figure 9:
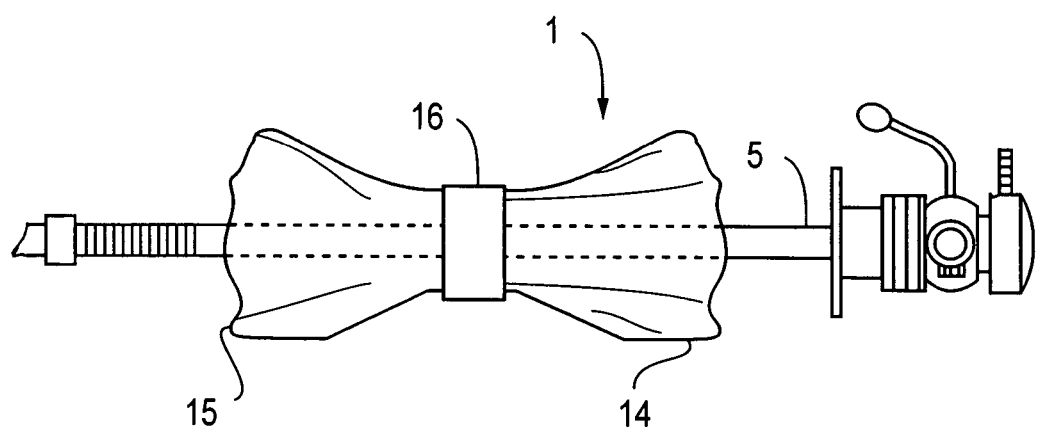
FIG. 9 illustrates the flexible tubular sheath of FIG. 1 housed in the center of an endoscopic instrument and with a black tape over the middle region of the system.

When an endoscopic instrument housing with a flexible tubular sheath passes into the tissue cavity opening, an indentation is created over the outer surface of the flexible tubular sheath cavity because the walls of the tissue cavity opening press over the flexible tubular sheath cavity 4. Referring to FIG. 9, a black adhesive tape is applied around the flexible tubular sheath disposed on the endoscopic instrument 5, so that an indentation is produced on the outer surface of the flexible tubular sheath cavity. The flexible tubular sheath has two distinct bulges, distal and proximal to the point of application of the tape. These bulges are termed the distal flexible tubular sheath bulge 15 and the proximal flexible tubular sheath bulge 14, respectively. The indentation produced as a result of a relatively tight application of the tape is symbolic of the impingement caused by the tissue cavity opening upon the flexible tubular sheath and this site of impingement is termed "indentation site" 16 (FIGS. 10B-10D). Thus, the distal flexible tubular sheath bulge and the proximal flexible tubular sheath bulge are invariably present on two sides of an indentation site.

Even if a relatively small volume of fluid were to be present inside the flexible tubular sheath cavity 4, the impingement at the indentation site could be enough to avoid cavity leakage, but it may not be enough to guarantee rolling motion for the flexible tubular sheath. If the outer surface 3 is made rough in the prospective site of indentation, a more effective grip could be established between the outer surface 3 and the tissue cavity opening and this could guarantee a rolling motion for the flexible tubular sheath even if relatively less fluid was present inside the flexible tubular sheath cavity 4. In an exemplary embodiment, the outer surface 3 could be made rough by incorporating small circular stipples on the outer surface. For example, parallel circular elevated ridges could be incorporated in the outer surface 3, such ridges lying in transverse plane at right angles to the long axis of the flexible tubular sheath. The parallel circular ridges should not be substituted by parallel longitudinal ridges, as the same would not establish an efficient grip between the outer surface of the flexible tubular sheath and the tissue cavity opening. Thus, a rough outer surface enhances the rolling motion for the flexible tubular sheath. As the flexible tubular sheath moves in a to and fro direction, the inner and the outer surfaces repeatedly interchange positions, meaning that the outer surface may also become the inner surface and vice versa. In the previous paragraphs it has been shown that the location of the indentation site should remain constant in relation to the outer surface. Thus, only that part of the outer surface needs to be made rough which is destined to be prospectively related to the indentation site.

Figure 10A:
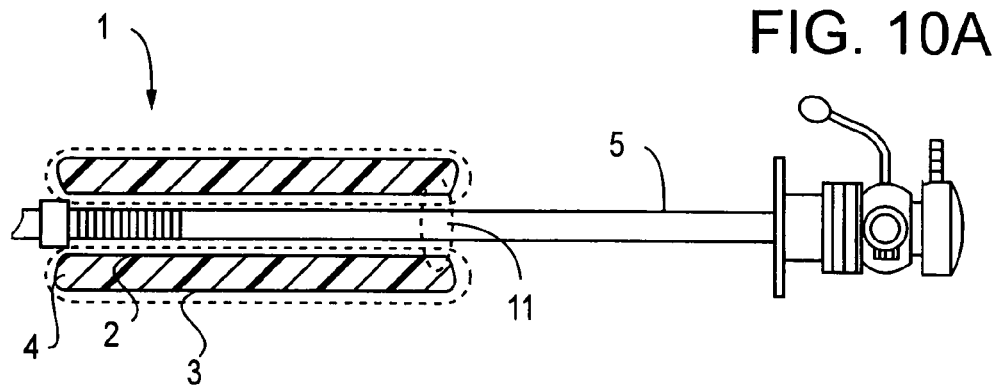
FIG. 10A illustrates a saggital section through an endoscopic instrument housing the flexible tubular sheath of FIG. 1 on its distal end.
Figure 10B:
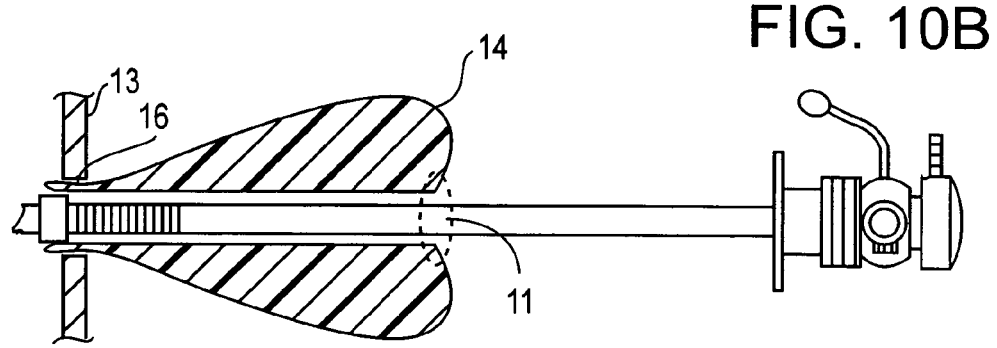
FIG. 10B illustrates the endoscopic instrument and flexible tubular sheath of FIG. 10A passing through a tissue cavity opening and according to a method of the present invention.
Figure 10C:
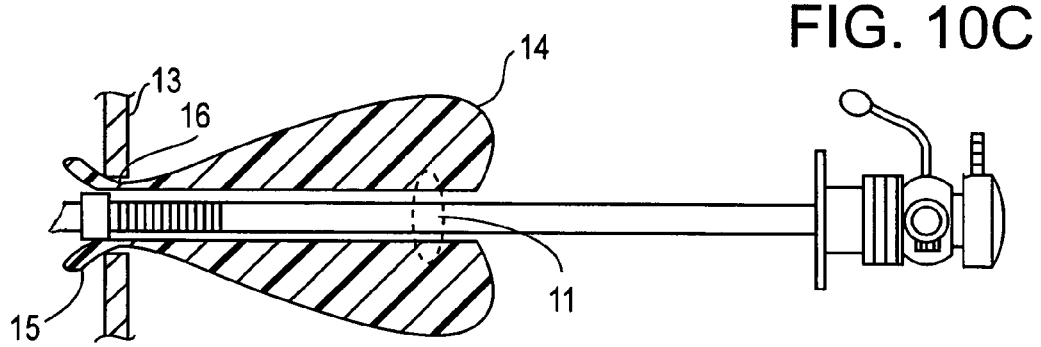
FIG. 10C illustrates the endoscopic instrument and flexible tubular sheath of FIG. 10A at a stage subsequent to that of FIG. 10B, and illustrating the formation of a distal flexible tubular sheath bulge.
Figure 10D:
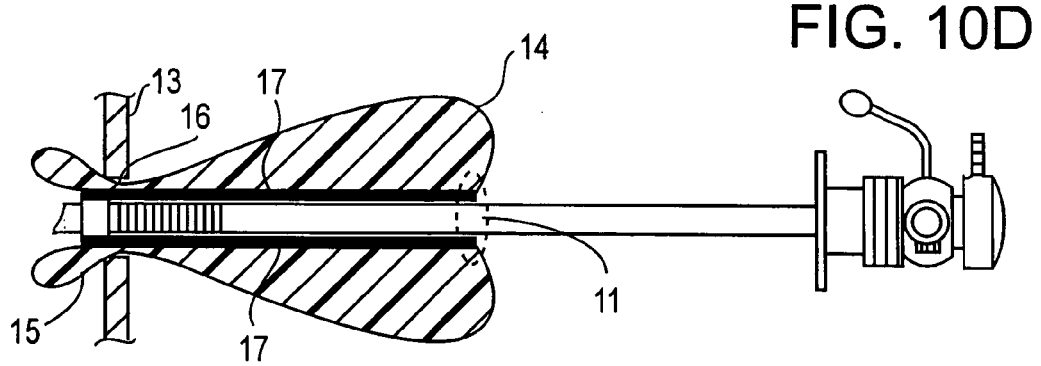
FIG. 10D illustrates the endoscopic instrument and flexible tubular sheath of FIG. 10A at a stage subsequent to that of FIG. 10C, and illustrating the longitudinal thickenings.

FIG. 10A shows flexible tubular sheath 1 installed over the distal part of endoscopic instrument 5. As noted, the term flexible tubular sheath refers to a flexible tubular sheath whose cavity 4 has been filled with a certain volume of fluid beyond which it would not be practically possible to pass an endoscopic instrument housing the flexible tubular sheath into the tissue cavity opening without deflating the flexible tubular sheath cavity. This certain volume of fluid is termed "lesser flexible tubular sheath cavity volume." Dashed lines 12 (FIG. 10A) represent a flexible tubular sheath cavity which has been distended to a "maximum possible volume capacity," beyond which it may not be possible to distend the flexible tubular sheath cavity any more from a practical point of view, and beyond which the flexible tubular sheath cavity pressure rises steeply and beyond which the flexible tubular sheath cavity could even burst. The maximum possible volume capacity is termed "maximum flexible tubular sheath cavity volume." From a practical point of view, the term "maximum flexible tubular sheath cavity volume" relates to a fluid volume beyond which the surgeon finds it practically difficult to distend the flexible tubular sheath cavity, i.e., if the surgeon were to manually do the same on his own. The concept "maximum flexible tubular sheath cavity volume" could exist only if the flexible tubular sheath cavity was made of a sufficiently thick, strong and elastic polymeric material. If the flexible tubular sheath cavity was made up of a relatively thinner, a weaker elastic material, then the relevance of the concept "maximum flexible tubular sheath cavity volume" would be greatly reduced. An endoscopic instrument housing a flexible tubular sheath cavity filled to a "maximum flexible tubular sheath cavity volume" cannot be pushed through a narrow tissue cavity opening. Also, any flexible tubular sheath cavity volume smaller than the "maximum flexible tubular sheath cavity volume" at which the endoscopic instrument could be directly introduced through the tissue cavity opening is termed "lesser flexible tubular sheath cavity volume." FIG. 10B shows an endoscopic instrument housing a flexible tubular sheath distended to a lesser flexible tubular sheath cavity volume being pushed through a tissue cavity opening 13. The inner walls of the tissue cavity opening 13 squeeze the distal end of the flexible tubular sheath at the indentation site 16.

Referring to FIG. 10C, as the endoscopic instrument is pushed further into the tissue cavity opening 13, the pressure inside the proximal flexible tubular sheath bulge increases, as a result of which some fluid is squeezed in the direction of the distal end of the flexible tubular sheath cavity, so that a distal flexible tubular sheath bulge 15 develops. In such case, it is always possible to completely withdraw the endoscopic instrument out of the tissue cavity opening 13 as the sequence of events stated above could also be replicated in an opposite manner. In this situation, the endoscopic instrument could always be withdrawn or accidentally come out of the tissue cavity opening. However, some surgeons might not like the endoscopic instrument to accidentally totally come out of the tissue cavity opening. The solution to this problem is shown in FIG. 10D. The rigid thickening 11 is located at the proximal most part of the flexible tubular sheath in FIGS. 10B, 10C and 10D. However, in FIGS. 10B and 10C, the flexible tubular sheath is distended to a "lesser flexible tubular sheath cavity volume," thus it could be directly introduced and removed from the tissue cavity opening. In FIG. 10D, the flexible tubular sheath cavity was initially filled to a "lesser flexible tubular sheath cavity volume," so that the endoscopic instrument could be pushed through the tissue cavity opening after which the total quantity of fluid inside the flexible tubular sheath cavity was increased to some volume at which the flexible tubular sheath housed on the endoscopic instrument is unable to be withdrawn totally from the tissue cavity opening 13. This volume is termed "anchoring flexible tubular sheath cavity volume." After attaining the anchoring flexible tubular sheath cavity volume, any attempt to pull out the endoscopic instrument from the tissue cavity opening 13 tends to compress the proximal flexible tubular sheath bulge 14, which leads to an increased pressure inside the proximal flexible tubular sheath bulge thus forcing some fluid from the proximal flexible tubular sheath bulge to escape into the distal flexible tubular sheath bulge, all of which culminates in an increase in the size of the proximal flexible tubular sheath bulge. Thus, the dilated proximal flexible tubular sheath bulge is unable to totally come out of a relatively narrow tissue cavity opening. The "anchoring flexible tubular sheath cavity volume" is greater than the "lesser flexible tubular sheath cavity volume" and smaller than the "maximum flexible tubular sheath cavity volume." It is also noted that, at the "maximum flexible tubular sheath cavity volume" or beyond a rolling motion, is not possible as an adequate indentation site cannot be established due to a permanent overall convexity of the outer flexible tubular sheath surface.

If the tissue cavity opening fits tightly at the indentation site, by tightly impinging all around the outer surface of the flexible tubular sheath at indentation site, then the fluid escaping from the proximal flexible tubular sheath bulge to the distal flexible tubular sheath bulge or vice versa could encounter considerable resistance to its flow, as a result of which the proximal flexible tubular sheath bulge and the distal flexible tubular sheath bulge could require a relatively greater time and physical effort in filling or emptying. The surgeon could thus find it uncomfortable to maneuver the endoscopic instrument in and out of the tissue cavity opening. To overcome this problem, two different methods are set forth below.

Referring to FIG. 10D, a limited length of the inner surface has been deliberately represented by thick lines 17. The thick line 17 represents an area of the inner surface which can come in apposition with the indentation site. Area 17 of the inner surface can contain longitudinal elevated ridges which do not allow the inner and the outer surface of the flexible tubular sheath cavity to come in complete apposition with each other at the indentation site. This facilitates the exchange of fluid between the distal flexible tubular sheath bulge and the proximal flexible tubular sheath bulge. The longitudinal ridges are preferably longitudinal thickenings along the inner surface which project into the flexible tubular sheath cavity 4. The longitudinal thickenings project towards the flexible tubular sheath cavity 4 and are not be incorporated between the inner surface of the flexible tubular sheath cavity 4 and the external surface of the endoscopic instrument 5. The width and depth of the longitudinal thickenings can be adjusted to suit the operational needs of an endoscopic procedure. Similarly, the separation between the longitudinal thickenings can also be adjusted to suit the operational needs. As the longitudinal thickenings lie over the inner aspect of the flexible tubular sheath cavity 4, they never rub against the tissue cavity opening 13.

In an exemplary embodiment, the flexible tubular sheath cavity 4 is filled with a fluid having lubricating properties. The lubricating nature of such fluid reduces the friction between the inner and the outer surfaces at the indentation site during rolling motion of the flexible tubular sheath. This not only increases the maneuverability in the to and fro direction, but also enhances the rotatory motion of the endoscopic instrument. The fluid having lubricating properties can be a physiological oily substance such as linolenic acid, linolic acid or arachiodenic acid. The fluid which has lubricating properties can also be a semi physiological oily substance, such as sunflower oil or ground nut oil. The fluid which has lubricating properties can also be xylocaine jelly which is commonly used in surgical procedures. Although xylocaine jelly is extremely viscous, it can be used beneficially in certain endoscopic procedures such as endometrial resection, where extreme stability of the endoscopic instrument is required in certain maneuvers such as while resecting the intra mural part of the fallopian tubes. The cavity fluid is preferably physiological in nature because if the flexible tubular sheath cavity accidentally bursts then the fluids may come in contact with body tissues. Similarly, the cavity 4 fluid is also preferably sterile.

It is possible that the endoscopic instrument could accidentally enter abnormally deep inside the tissue cavity and, thus, accidentally perforate the tissue cavity. To avoid this serious complication, a rigid thickening similar to 11 may also be incorporated in a distal part of the inner surface of the flexible tubular sheath cavity. Such a rigid thickening would not allow the endoscopic instrument to enter into the tissue cavity beyond a predetermined depth, the mechanism for which has already been described in the preceding paragraphs. Also the exact location of such distally located rigid thickening depends upon the cavity depth.

Referring back to FIG. 10D, to introduce fluid or extra fluid inside the flexible tubular sheath cavity, a separate small caliber delivery tube could be connected to the flexible tubular sheath cavity 4. A suitable site for connecting such a tube could be at a location just distal to the rigid thickening 11, so that the tube passes between the inner surface of the flexible tubular sheath and the external surface of the endoscopic instrument to reach the location. The proximal open end of such tube could be provided with a controllable valve, which would prevent the flexible tubular sheath cavity fluid from escaping during an endoscopic procedure. A tube for introducing fluid into the flexible tubular sheath cavity is termed the "cavity filling tube" (not shown).

The surgeon could perform an entire endoscopic procedure by using a flexible tubular sheath cavity which has already been predistended to a lesser flexible tubular sheath cavity volume. Alternatively, the surgeon may initially introduce a flexible tubular sheath cavity distended to a lesser flexible tubular sheath cavity volume and later introduce extra fluid via the cavity filling tube to attain anchoring flexible tubular sheath cavity volume.

The thickness, strength and elasticity of the polymeric material constituting the flexible tubular sheath cavity may be chosen according to the operational needs of the endoscopic procedure. In relatively delicate cavities like the uterine cavity, the polymeric material could be relatively thin and elastic. In tough cavities, like the joint cavity, the polymeric material should preferably be thicker and stronger. The flexible tubular sheath cavity can contain any fluid (i.e., liquid or gas), depending on the surgeon's choice and the endoscopic procedure. Further, the fluid may have various degrees of viscosity. Certain maneuvers like resecting the intramural part of the fallopian tubes require great precision. Such maneuvers may be benefited by choosing high viscosity fluids for the flexible tubular sheath cavity. Some endoscopic instruments have multiple holes at their distal end just adjacent to the tip of the endoscopic instrument. Such holes help in extracting waste fluid during continuous flow irrigation. Preferably, the flexible tubular sheath is deployed so that these holes never get covered.

The system for managing a lquid or gas distending medium of the present invention is a hollow double walled, pressurized, cylindrical body movable by a rolling type of motion. The system of the present invention is used for minimizing and regulating the leakage of liquid or gaseous distending media by the sides of the endoscopic instrument, such that the entire maneuver also enhances the maneuverability of the endoscopic instrument.

The system greatly enhances the efficiency and patient safety in various endoscopic procedures, by minimizing or avoiding the leakage of the distending medium by the sides of the endoscopic instrument.

Although the present invention has been described in relation to particular embodiments thereof, many other variations and modifications and other uses will become apparent to those skilled in the art.

What is claimed as new and desired to be protected by Letters Patent of the United States is:

1. A method of managing a distending medium during an endoscopic procedure, comprising:
   providing a flexible tubular sheath having a proximal end and a distal end, the flexible tubular sheath consisting of a flexible double-wall cylindrical structure formed of walls that are all flexible, the flexible walls defining a closed, flexible cavity, the closed, flexible cavity being permanently filled and consisting of a constant, predetermined volume of fluid and having a uniform inner diameter throughout its length;
   subsequently, installing the entire flexible tubular sheath over a limited longitudinal portion of an endoscopic instrument, so that the entire flexible tubular sheath surrounds and is in contact with a specific location of the endoscopic instrument; and
   after the step of installing the entire flexible tubular sheath over the limited longitudinal portion of the endoscopic instrument, introducing the endoscopic instrument together with the installed flexible tubular sheath into a body cavity through an incision in a wall of the body cavity and through a rolling motion, so that the flexible tubular sheath is partially inserted into the body cavity during the endoscopic procedure to allow insertion of additional instruments through it, and so that outer and inner surfaces of the flexible double-wall cylindrical structure interchange their position by rolling motion and the distal end of the flexible tubular sheath inside the body cavity acquires a bell shape, to prevent leakage of the distending medium from the body cavity through the incision,
   wherein only a limited portion of the flexible tubular sheath that is in close proximity to the distal end is in contact with the wall of the body cavity and wherein a length of the said limited portion is equal to the wall thickness of the body cavity.

2. The method of claim 1, wherein the cavity is filled with a mixture of a liquid and a gas.

3. The method of claim 1, wherein the cavity is filled with a fluid having lubricating properties.

4. The method of claim 1, wherein the double-wall cylindrical structure is formed of an elastic material.

5. The method of claim 4, wherein the elastic material is an elastic polymeric material.

6. The method of claim 1, wherein the flexible tubular sheath is provided with a plurality of ridges.

7. The method of claim 1, wherein the endoscopic instrument is selected from the group consisting of endoscopes, shavers, scissors, forceps, tissue retractors, probes and electrodes.

8. A method of preventing leakage of a distending medium around at least a side of an endoscopic instrument, the method comprising the steps of:
   providing a flexible tubular sheath having a proximal and a distal end, the flexible tubular sheath consisting of a flexible double-wall cylindrical structure formed of walls that are all flexible, the flexible walls defining a closed, flexible cavity that is permanently filled and consisting of a constant, predetermined volume of fluid which is not totally or partially removed and having a uniform inner diameter throughout its length;
   subsequently, installing the entire flexible tubular sheath over a limited part of the endoscopic instrument so that the entire flexible tubular sheath surrounds and is in contact with a specific location of the endoscopic instrument; and
   after the step of installing the entire flexible tubular sheath over the limited part of the endoscopic instrument, introducing the endoscopic instrument together with the installed closed, flexible tubular sheath into a body cavity through an incision in a wall of the body cavity and through a rolling motion so that the flexible tubular sheath is partially inserted into the body cavity during the endoscopic procedure to allow insertion of additional instruments through it, and so that outer and inner surfaces of the flexible double-wall cylindrical structure interchange their position by rolling motion and the distal end of the flexible tubular sheath inside the body cavity acquires a bell shape, to prevent leakage of the distending medium from the body cavity through the incision,
   wherein only a limited portion of the flexible tubular sheath that is in close proximity to the distal end is in contact with the wall of the body cavity and wherein a length of the said limited portion is equal to the wall thickness of the body cavity.

9. The method of claim 8, wherein the double-wall cylindrical structure is formed of an elastic material.

10. The method of claim 9, wherein the elastic material is a polymeric elastic material.

11. The method of claim 8, wherein the cavity is filled with a fluid having lubricating properties.

12. A method of managing a distending medium during an endoscopic procedure, comprising:
   providing a flexible tubular sheath having a proximal and a distal end, the flexible tubular sheath consisting of a flexible double-wall cylindrical structure formed of walls that are all flexible, the flexible walls defining a closed, flexible cavity, the closed, flexible cavity being permanently filled and consisting of a constant, predetermined volume of fluid and having a uniform inner diameter and a uniform outer diameters throughout its length;
   subsequently, installing the entire flexible tubular sheath over a limited longitudinal portion of an endoscopic instrument, so that the flexible tubular sheath surrounds and is in contact with a specific location of the endoscopic instrument; and
   after the step of installing the entire flexible tubular sheath over the limited longitudinal portion of the endoscopic instrument, introducing the endoscopic instrument together with the installed flexible tubular sheath into a body cavity through an incision in a wall of the body cavity and through a rolling motion so that the flexible tubular sheath is partially inserted into the body cavity during the endoscopic procedure to allow insertion of additional instruments through it, and so that outer and inner surfaces of the flexible double-wall cylindrical structure interchange their position by rolling motion and the distal end of the flexible tubular sheath inside the body cavity acquires a bell shape, to prevent leakage of the distending medium from the body cavity through the incision,
   wherein only a limited portion of the flexible tubular sheath that is in close proximity to the distal end is in contact with the wall of the body cavity and wherein a length of the said limited portion is equal to the wall thickness of the body cavity.

13. A method of preventing leakage of a distending medium around at least a side of an endoscopic instrument, the method comprising the steps of:
   providing a flexible tubular sheath having a proximal end and a distal end, the flexible tubular sheath consisting of a flexible double-wall cylindrical structure formed of walls that are all flexible, the flexible walls defining a closed, flexible cavity that is permanently filled and consisting of a constant, predetermined volume of fluid which is not totally or partially removed and having a uniform inner diameter and a uniform outer diameters throughout its length;
   subsequently, installing the entire flexible tubular sheath over a limited part of the endoscopic instrument so that the entire flexible tubular sheath surrounds and is in contact with a specific location of the endoscopic instrument; and
   after the step of installing the entire flexible tubular sheath over the limited part of the endoscopic instrument, introducing the endoscopic instrument together with the installed closed, flexible tubular sheath into a body cavity through an incision in a wall of the body cavity and through a rolling motion so that the flexible tubular sheath is partially inserted into the body cavity during the endoscopic procedure to allow insertion of additional instruments through it, and so that outer and inner surfaces of the flexible double-wall cylindrical structure interchange their position by rolling motion and the distal end of the flexible tubular sheath inside the body cavity acquires a bell shape, to prevent leakage of the distending medium from the body cavity through the incision,
   wherein only a limited portion of the flexible tubular sheath that is in close proximity to the distal end is in contact with the wall of the body cavity and wherein a length of the said limited portion is equal to the wall thickness of the body cavity.

* * * * *